(12) United States Patent
Tanklevsky et al.

(10) Patent No.: US 6,306,645 B1
(45) Date of Patent: Oct. 23, 2001

(54) CONTAINER FOR EXPLANT CULTURE, METHOD OF USING SAME, AND PROCESS, MOLD AND APPARATUS OF MAKING SAME

(75) Inventors: Alexander Tanklevsky, Rehovot; Michael Tanklevsky, Dimona; Alla Tanklevsky, Rehovot, all of (IL)

(73) Assignee: Incell Ltd., Rehovot (IL)

( * ) Notice: Subject to any disclaimer, the term of this patent is extended or adjusted under 35 U.S.C. 154(b) by 0 days.

(21) Appl. No.: 09/339,870

(22) Filed: Jun. 25, 1999

(51) Int. Cl.[7] .................................................. C12M 1/12
(52) U.S. Cl. ..................... 435/297.1; 435/297.5; 435/305.2; 435/305.3
(58) Field of Search .............. 435/297.1, 299.5, 435/305.2, 305.3; 47/62–64, 65.5, 901

(56) References Cited

U.S. PATENT DOCUMENTS

| | | | | |
|---|---|---|---|---|
| 4,000,580 | * | 1/1977 | Biehl ......................................... | 47/14 |
| 5,119,588 | * | 6/1992 | Timmis et al. ........................... | 47/58 |
| 5,212,906 | * | 5/1993 | Okuno et al. ............................ | 47/62 |
| 5,525,505 | * | 6/1996 | Young et al. ...................... | 435/240.4 |
| 5,842,310 | * | 12/1998 | Liu et al. ................................. | 47/59 |

* cited by examiner

Primary Examiner—David A. Redding
(74) Attorney, Agent, or Firm—Mark M. Friedman

(57) ABSTRACT

An improved device, in the form of a container, for propagating explant cultures under sterile conditions while facilitating gas exchange with an outside environment, methods for employing the device, a process of manufacture to produce the device, a mold for use as part of the process of manufacture, and an apparatus for conducting the process of manufacture employing the mold.

3 Claims, 7 Drawing Sheets

CONTAINER FOR EXPLANT CULTURE, METHOD OF USING SAME, AND PROCESS, MOLD AND APPARATUS OF MAKING SAME

FIELD AND BACKGROUND OF THE INVENTION

The present invention relates to the growth of cells under sterile conditions, especially explant cultures of plants. More particularly, the present invention relates to (i) novel and improved containers for containing and nurturing explant cultures; (ii) methods of growing plants in explant culture employing the aforesaid containers; (iii) molds for manufacturing the aforesaid containers; (iv) methods of manufacturing the aforesaid containers using the molds; and to (v) apparatuses employing the molds for manufacturing the aforesaid containers.

The present invention is intended to facilitate large scale propagation of plants commonly grown in cell culture and further to allow their distribution from a central facility to planting areas remote from the facility. Plants suited to use with the proposed invention include, but are not limited to, bananas, cassavas, strawberries, potatoes, beets, onions, and orchids and other ornamental flowers and food crops. Similarly, the present invention may find used in cultures of animal cells or in culture of embryos from pluripotent animal cell lines.

The present invention is designed to allow efficient low cost production of uniform plants, and to facilitate such production by unskilled personnel in facilities with a minimum of equipment. Further, the present invention is designed to facilitate transfer of plants grown in explant culture to the soil while minimizing root damage and other types of trauma to the plant.

The prior art teaches a number of devices for plant germination and propagation.

One prior art device, disclosed in U.S. Pat. No. 1,279,310 is designed only for assaying viability of seed samples, and not for facilitating their further cultivation.

Similarly, U.S. Pat. Nos. 2,571,491; 2,323,746; 5,27,951 and 526,512 teach a number of methods for planting seeds between sheets or strips of porous material. These patents all deal with devices and methods for predetermining the spacing and orientation of seeds prior to planting in a field. U.S. Pat. No. 4,910,911 teaches a similar device designed to contain young plants instead of seeds. While reference is made in these patents to inclusion of nutrients or fertilizers, application of such materials is continuous throughout the growing period from the time of planting until the material is depleted. If changes in concentration of specific components of a nutrient or fertilizer occur, they are reduction over time. Delayed delivery of a nutrient mixture therefore requires application to the growing plants from a source outside the patented device. All of these inventions are also designed to disintegrate over time, releasing seeds or plants contained therein into the soil. Most relevant to the present invention, none of these prior art patents insure sterility of seeds or plants during early stages of growth.

Additional prior art devices for propagating and growing plants are disclosed in U.S. Pat. Nos. 3,172,234 and 5,081, 791. These devices are not dissolvable in soil, but require either inclusion of all required nutrients in a rooting medium, or addition of nutrients from an outside source. As with aforesaid prior art devices, no provision for sterile cultivation is made in these devices.

All of the aforesaid prior art devices are designed for use with seeds or young plants, not for use with cells from explant culture.

An additional prior art device is disclosed in U.S. Pat. No. 4,000,580. This device makes no provision for sterility during growth and is designed for small-scale experiments employing seeds, not for commercial scale propagation of explant cultures.

Additional prior art devices exist for use in plant culture facilities. One such device is disclosed in U.S. Pat. No. 5,335,345. This device is designed specifically for transferring plants grown in culture from one container to another. U.S. Pat. No. 5,212,906 teaches a device for growth of plants under sterile conditions. This device is specifically designed for use with plant bodies and requires the use of external nutrient supplies and gas supplies. An additional prior art device is disclosed in U.S. Pat. No. 5,525,505. This device can be used to incubate plant material in individual plastic chambers, which are then placed in tray of liquid nutrient broth. This arrangement requires special provisions for keeping the nutrient broth, which is external to the growth chamber, free of contaminants.

There is thus a widely recognized need for, and it would be extremely advantageous to have, a container for propagating cell culture material under sterile conditions which facilitates addition or change of culture medium, or specific components thereof, from a source within the container, but separate from the incubation chamber.

SUMMARY OF THE INVENTION

According to one aspect of the present invention there is provided a device for propagating explant cultures, the device comprising (a) at least one growth chamber for containing and retaining therein a culture medium; (b) at least one supplements reservoir for containing and retaining therein at least one supplementary substance, the at least one supplements reservoir being in fluid communication with the at least one growth chamber, such that, when so required, the at least one supplementary substance is addable to the at least one growth chamber; and (c) at least one labyrinthine channel communicating between the at least one growth chamber and an atmosphere.

According to further features in preferred embodiments of the invention described below, the at least one growth chamber, the at least one supplements reservoir and the at least one labyrinthine channel are realized between a first plastic sheet formed with cavities therein defining the at least one growth chamber, the at least one supplements reservoir and the at least one labyrinthine channel and a second, flat, plastic sheet scaled thereto, so as to form the at least one growth chamber, the at least one supplements reservoir and the at least one labyrinthine channel.

According to still further features in the described preferred embodiments the first plastic sheet and the second plastic sheet are sealed so as to form the at least one growth chamber, the at least one supplements reservoir and the at least one labyrinthine channel via a seal formed by welding, bonding or soldering.

According to still further features in the described preferred embodiments the first plastic sheet is constructed such that each of the at least one growth chamber and each of the at least one supplements reservoir is adapted for holding a liquid therein when the first plastic sheet is vertically positioned and when the second, flat, plastic sheet is yet unsealed thereto.

According to still further features in the described preferred embodiments the first plastic sheet is constructed such that each of the at least one growth chamber and each of the at least one supplements reservoir is adapted for holding a liquid therein when the first plastic sheet is horizontally positioned and when the second, flat, plastic sheet is yet unsealed thereto.

According to another aspect of the present invention there is provided a method for propagating explant cultures comprising the steps of (a) providing a first sheet formed with cavities therein defining at least one growth chamber, at least one supplements reservoir and a labyrinthine channel, being in fluid communication with one another; (b) placing a growth medium in the at least one growth chamber; (c) placing at least one supplementary substance in the at least one supplements reservoir; (d) providing biological material in the culture medium; (e) sealing a second sheet over the first sheet; and (f) following a time period, supplementing the growth medium with at least one of the supplementary substance while avoiding separation between the first and second sheets.

According to still further features in the described preferred embodiments the step of sealing the second sheet over the first sheet is effected by a sealing process selected from the group consisting of welding, bonding or soldering.

According to still further features in the described preferred embodiments the step of supplementing said growth medium with at least one of said supplementary substance while avoiding separation between said first and second sheets is effected in a series of successive supplementations.

According to yet another aspect of the present invention there is provided a device for propagating explant cultures, the device comprising (a) at least one growth chamber for containing and retaining therein a culture medium; and (b) a gas permeable, liquid impermeable membrane sealing the at least one growth chamber.

According to further features in preferred embodiments of the invention described below, the device further comprising at least one supplements reservoir for containing and retaining therein at least one supplementary substance, the at least one supplements reservoir being in fluid communication with the at least one growth chamber, such that, when so required, the at least one supplementary substance is addable to the at least one growth chamber.

According to still further features in the described preferred embodiments there is provided an assembly comprising a plurality of units each of the plurality of units includes a device as set forth above.

According to still further features in the described preferred embodiments at least some of the plurality of units are separated therebetween via perforations.

According to still further features in the described preferred embodiments the gas permeable, liquid impermeable membrane and the at least one growth chamber are sealed via a seal formed by welding, bonding or soldering.

According to still further features in the described preferred embodiments the is constructed such that each of the at least one growth chamber is adapted for holding a liquid therein when vertically positioned and when the gas permeable, liquid impermeable membrane, is yet unsealed thereto.

According to still further features in the described preferred embodiments the device is constructed such that each of the at least one growth chambers is adapted for holding a liquid therein when horizontally positioned and when the gas permeable, liquid impermeable membrane, is yet unsealed thereto.

According to still another aspect of the present invention there is provided a method for propagating explant cultures comprising the steps of (a) providing at least one growth chamber; (b) placing a growth medium in the at least one growth chamber; (d) providing biological material in the culture medium; and (e) sealing the at least one growth chamber with a gas permeable, liquid impermeable membrane.

According to still further features in the described preferred embodiments the method further comprising the steps of (f) providing at least one supplements reservoir being in fluid communication with the at least one growth chamber; (g) placing at least one supplementary substance in the at least one supplements reservoir, wherein the step of sealing the at least one growth chamber with the gas permeable, liquid impermeable membrane is effected so as to seal also the least one supplements reservoir with the gas permeable, liquid impermeable membrane; and (h) following a time period, supplementing the growth medium with at least one of the supplementary substances while the gas permeable, liquid impermeable membrane remains sealed and intact.

According to still further features in the described preferred embodiments the step of sealing the at least one growth chamber with a gas permeable, liquid impermeable membrane is effected by a sealing process selected from the group consisting of welding, bonding or soldering.

According to still further features in the described preferred embodiments the step of supplementing the growth medium with at least one of the supplementary substance while allowing the seal to remain intact is effected in a series of successive supplementations.

According to an additional aspect of the present invention there is provided a device for propagating explant cultures, the device comprising (a) a plate having a first circumference profile and being formed with (i) at least one growth chamber for containing and retaining therein a culture medium; (ii) at least one supplements reservoir for containing and retaining therein at least one supplementary substance, the at least one supplements reservoir being in fluid communication with the at least one growth chamber, such that, when so required, the at least one supplementary substance is addable to the at least one growth chamber; and (b) a cover for covering the plate, the cover being formed with a second circumference profile, the first circumference profile and the second circumference profile being constructed so as to form a circumferential labyrinthine passage between the plate and the cover when the plate is covered by the cover, the circumferential labyrinthine passage communicating between the at least one growth chamber and an atmosphere.

According to still further features in the described preferred embodiments the cover is attached to the container by means of an integral hinge.

According to still further features in the described preferred embodiments the cover is separable from the plate.

According to still further features in the described preferred embodiments the at least one growth chamber contains therein the culture medium According to still further features in the described preferred embodiments the at least one growth chamber includes a plurality of growth chambers, whereas the plurality of growth chambers are in fluid communication with one another through medium non-containing portions thereof.

According to still further features in the described preferred embodiments the at least one growth chamber includes a plurality of growth chambers, whereas the plurality of growth chambers are in fluid communication with one another through medium containing portions thereof.

According to yet additional aspect of the present invention there is provided a method for propagating explant cultures comprising the steps of (a) providing a plate formed with at least one growth chamber and at least one supplements reservoir being in fluid communication with one another; (b) placing a growth medium in the at least one growth chamber; (c) placing at least one supplementary substance in the at least one supplements reservoir; (d) providing biological material in the at least one culture medium; (e) covering the plate with a cover so as to form a circumferential labyrinthine passage between the plate and the cover, the circumferential labyrinthine passage communicating between the at least one growth chamber and an atmosphere; and (f) following a time period, supplementing the growth medium with at least one of the supplementary substance while avoiding removing the cover from the plate.

According to still further features in the described preferred embodiments the method further comprising the step of placing a plant support matrix along with the growth medium in the at least one growth chamber. Thus, according to still further features in the described preferred embodiments the at least one growth chamber includes a plant support matrix therein.

According to still further features in the described preferred embodiments the plant support matrix is selected from the group consisting of agar, agarose, absorbent gel, absorbent particles, a polyurethane foam, a non-woven polypropylene fiber, polypropylene netting, glass beads, a microporous polypropylene membrane, a polypropylene netting, polyacrylamide beads, super absorbent gel, vermiculite, stonewool, paper and soil.

According to still further features in the described preferred embodiments the at least one supplementary substance is selected from the group consisting of antibacterial agent, antiviral agent, antifungal agent, the growth medium, a different growth medium and a mineral solution including at least one mineral.

According to still an additional aspect of the present invention there is provided a process of manufacturing a device for propagating explant cultures, the process comprising the steps of (a) providing a plastic material; and (b) forcing the plastic material to conform with a contour of a mold, thereby defining at least one growth chamber, at least one supplements reservoir and at least one labyrinthine channel being in fluid communication with one another.

According to further features in preferred embodiments of the invention described below, the step of forcing the plastic material to conform with the contour of the mold is effected by a method selected from the group consisting of vacuum or pressure thermoforming, roller pressing, injection molding and pressing between matching molds.

According to still further features in the described preferred embodiments heat is applied to the plastic material while forcing the plastic material to conform with the contour of the mold.

According to another aspect of the present invention there is provided a mold for manufacturing a device for propagating explant cultures, the mold comprising a flat body being formed with a plurality of patterns being in communication with one another, the plurality of patterns are so designed such that by placing a plastic sheet on top of the flat body and forcing portions of the plastic sheet to conform with the plurality of patterns, the plastic sheet deforms to thereby define at least one growth chamber, at least one supplements reservoir and at least one labyrinthine channel in fluid communication with one another.

According to yet another aspect of the present invention there is provided an apparatus for manufacturing a device for use in explant culture, the apparatus comprising (a) a mold having a flat body being formed with a plurality of patterns being in communication with one another, the plurality of patterns are so designed such that by placing a plastic sheet on top of the flat body and forcing portions of the plastic sheet to conform with the plurality of patterns, the plastic sheet deforms to thereby define at least one growth chamber, at least one supplements reservoir and at least one labyrinthine channel in fluid communication. with one another; and (b) a mechanism operating with the mold for forcing the portions of the plastic sheet to conform with the plurality of patterns.

According to still another aspect of the present invention there is provided a process of manufacturing a device for propagating explant cultures, the process comprising the steps of (a) providing a plastic material; and (b) forcing the plastic material to conform with a contour of a mold, thereby defining at least one growth chamber and at least one supplements reservoir being in fluid communication with one another.

According to still further features in the described preferred embodiments the step of forcing the plastic material to conform with the contour of the mold is effected by a method selected from the group consisting of vacuum or pressure thermoforming, roller pressing, injection molding and pressing between matching molds.

According to still further features in the described preferred embodiments heat is applied to the plastic material while forcing the plastic material to conform with the contour of the mold.

According to an additional aspect of the present invention there is provided a mold for manufacturing a device for propagating explant cultures, the mold comprising a flat body being formed with a plurality of patterns being in communication with one another, the plurality of patterns are so designed such that by placing a plastic sheet on top of the flat body and forcing portions of the plastic sheet to conform with the plurality of patterns, the plastic sheet deforms to thereby define at least one growth chamber and at least one supplements reservoir in fluid communication with one another.

According to yet additional aspect of the present invention there is provided an apparatus for manufacturing a device for use in explant culture, the apparatus comprising (a) a mold having a flat body being formed with a plurality of patterns being in communication with one another, the plurality of patterns are so designed such that by placing a plastic sheet on top of the flat body and forcing portions of the plastic sheet to conform with the plurality of patterns, the plastic sheet deforms to thereby define at least one growth chamber and at least one supplements reservoir in fluid communication with one another; and (b) a mechanism operating with the mold for forcing the portions of the plastic sheet to conform with the plurality of patterns.

According to still further features in the described preferred embodiments the patterns protrude from a surface of the flat body.

According to still further features in the described preferred embodiments the patterns recess from a surface of the flat body.

According to still further features in the described preferred embodiments the mechanism is selected from the group consisting of a pressure mechanism, a vacuum mechanism, a press mechanism and a heating mechanism.

The present invention successfully addresses the shortcomings of the presently known configurations by providing a low cost device for explant culture, which facilitates growth under sterile conditions and allows aseptic addition or change of culture medium without benefit of a laminar flow hood. Such a device allows performance of routine explant propagation by unskilled personnel in facilities with a minimum of equipment. Additionally, molds and methods for their use allow construction of the aforesaid device to be undertaken easily at or near the intended point of use.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
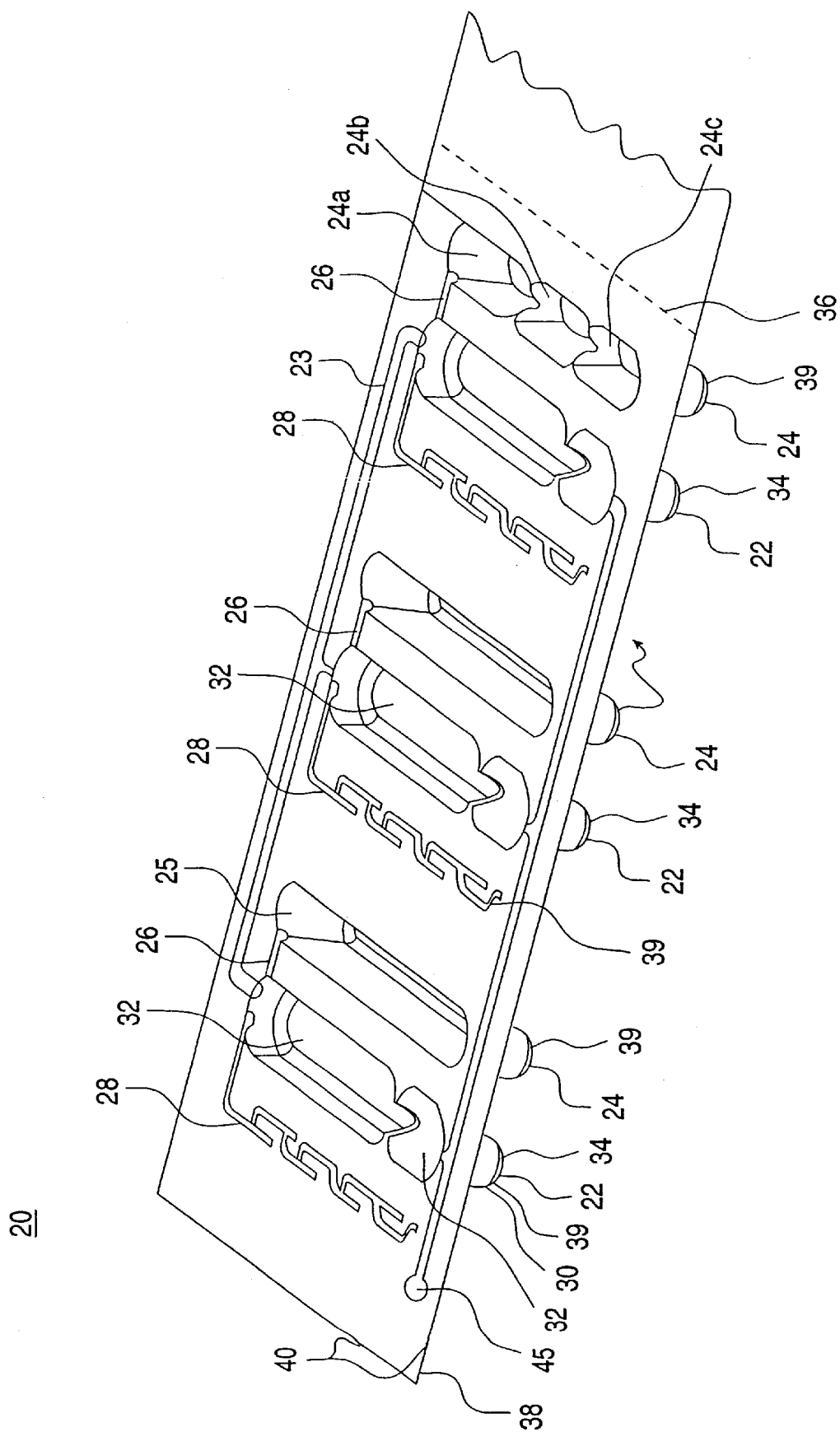
FIG. 1 is a perspective view of a device for propagating explant cultures according to one aspect of the present invention showing several additive or alternative embodiments which are not necessarily integrated into a single device.

The present invention is of an improved device, in the form of a container, for propagating explant cultures which can be employed to nurture the aforesaid cultures under sterile conditions while facilitating gas exchange with an outside environment. The function of gas exchange is accomplished by one of a number of mechanisms including, but not limited to a labyrinthine channel, circumferential labyrinthine passage, and/or a gas permeable, liquid impermeable membrane. This plurality of mechanisms for gas exchange allows the device of the present invention to have a variety of physical appearances while still retaining all of its functional characteristics. The present invention also encompasses a method for employing the device of the present invention to propagate explant cultures, processes of manufacture to produce the device of the present invention, a mold to be used as part of the aforesaid process of manufacture, and an apparatus for conducting the aforesaid process of manufacture employing the aforesaid mold.

Specifically, the present invention can be used to facilitate large scale propagation of plants commonly grown in cell culture and further to allow their distribution from a central facility to planting areas remote from the facility. Plants suited to use with the present invention include, but are not limited to, bananas, cassavas, strawberries, potatoes, beets, onions, and orchids and other ornamental flowers and food crops. Similarly, the present invention may find used in cultures of animal cells, animal cell lines or in culture of embryos from pluripotent animal cell lines. Suitability of the present invention for use with a specific cell type is unaffected by any genetic modifications which may have been previously performed on the cells to be propagated. Similarly, the device of the present invention may be applied to transfecting or transforming cells during propagation, or to regulating expression of specific genes in propagated cells via addition or removal of specific components of a culture medium during propagation.

Design features of the present invention allow efficient low cost production of uniform plants and facilitate such production by unskilled personnel in facilities with a minimum of equipment. In addition, the present invention is designed to facilitate transfer of plants grown in explant culture to the soil while minimizing root damage and other types of trauma to the plant.

The principles and operation of a device, in the form of a container, for propagating explant cultures, and of methods for using aforesaid device to propagate explant cultures, and of a process of manufacture to produce the aforesaid device, and of a mold to be used as part of the aforesaid process of manufacture, and of an apparatus for performing the aforesaid process of manufacture employing the aforesaid mold according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For purposes of this specification and the accompanying claims, the phrase "growth medium" includes a combination of nutrients. Such a combination can include, for example, a nitrogen source, a carbon source and/or minerals. A preferred growth medium which is useful for propagation of explants includes micro elements, such as, but not limited to, $CuSO_4$, $MnSO_4$, etc., macro elements, such as, but not limited to, $CaCl_2$, $KH_2PO_4$, $KNO_3$, $MgSO_4$, $NH_4NO_3$, etc., vitamins, such as, but not limited to, myo-inositol, thiamine, etc. A ready to use solution is available from Duchefa Biochemie BV, The Netherlands.

For purposes of this specification and the accompanying claims, the phrase "plant support matrix" includes, but is not limited to, agar, agarose, absorbent gel, absorbent particles, a polyurethane foam, a non-woven polypropylene fiber, polypropylene netting, glass beads, a microporous polypropylene membrane, a polypropylene netting, polyacrylamide beads, super absorbent gel, vermiculite, stonewool, paper and soil. It will be appreciated that in some cases the plant support matrix is homogeneously mixed with a growth medium.

For purposes of this specification and the accompanying claims, the phrase "supplementary substance" includes, but is not limited to antibacterial agents, antiviral agents, antifungal agents, additional growth medium, a growth medium with different composition, a hormone, a growth factor, DNA, RNA and a salt solution including at least one salt or mineral.

For purposes of this specification and the accompanying claims, the term "plastic" refers to any one of a number of semi-rigid thermally moldable materials including, but not limited to polyethylene terephthalate (PET), polypropylene (PP), high density polyethylene (HDPE), polyvinyl chloride (PVC) and acrylic (PMMA).

For purposes of this specification and the accompanying claims, the phrase "gas permeable, liquid impermeable, membrane" refers to a thin sheet of material which permits gas exchange but restricts entry of microbes such as bacteria and viruses while simultaneously preventing transfer of liquids, in water or water vapor, in particular, therethrough. An examples includes hydrophobic membranes such as, but not limited to, polytetrafluoroethylene (PTFE) filter, distributed, for example, by is Whatman Inc., Japan Millipore Ltd. or by Gelman Sciences Inc. Other hydrophobic membranes such as Isopore (a polyvinylpyrrolidone membrane, Japan Millipore Ltd.), a polyamide membrane (available from Sartorius AG), a nylon membrane (available from Corning Inc.), a cellulose acetate membrane and a cellulose nitrate membrane (available from Iwaki Glass Co., Ltd. and MF-Millipore), and a cellulose membran (evailable from Japan Millipore Ltd.) may also be employed, as well as Spunbonded olefin-TYVEK (DuPont) with or without coating.

For purposes of this specification and the accompanying claims, the term "sterilization" refers to processes including, but not limited to, irradiation, steam pressure, gas fumigation and chemical sterilization. For purposes of this specification and the accompanying claims, the term "production cycle" refers to a period typically greater than 28 but less than 35 days.

Referring now to the drawings, FIG. 1 illustrates a device for propagating explant cultures according to the present invention, which device is referred to hereinbelow as device 20. Device 20 includes at least one growth chamber 22 (a plurality, i.e., three chambers 22 are shown in FIG. 1) for containing and retaining therein a culture medium 32. Device 20 further includes at least one supplements reservoir 24 (three are shown) which serves for containing and retaining therein at least one supplementary substance 25 as defined hereinabove. Supplements reservoir(s) 24 are in fluid communication via channels 26 with growth chamber (s) 22, such that, when so required, the supplementary substance(s) are addable to growth chamber(s) 22. This is effected according to a preferred embodiment of the present invention by squeezing at least one of reservoir(s) 24 so as to force its contents via channels 26 into chambers 22. Device 20 further includes at least one labyrinthine channel 28 (three are shown) communicating between at least one growth chamber 22 and an atmosphere. According to a preferred embodiment of the present invention, at least some growth chamber(s) 22 retain a plant support matrix 30 as hereinabove defined. According to a preferred embodiment of the present invention, a plurality of growth chambers 22 are in fluid communication with one another through medium non-containing portions 32 thereof which serve for retaining the stem and leaves of a growing plant. Alternatively or additionally, a plurality of growth chambers 22 are in fluid communication with one another through medium containing portions 34 thereof, which serve for retaining, supporting an nourishing the plant roots.

It will be appreciated that any number of chambers 22, reservoirs 24 and channels 28 can be employed in device 10. Thus, for example, a single channel 28 and a single reservoir 24 can be used in fluid communication with a plurality of chambers 22. The minimal unit configuration, however, includes a single chamber 22, a single reservoir 24 and a single channels 28 are employed. Units, of minimal or which include any number of chambers 22, reservoirs 24 and channels 28 can be assembled into an assembly. Perforations 36 can be employed to assist in separating individual functional units if and when so desired.

According to a preferred embodiment of this aspect of the present invention growth chamber(s) 22, supplements reservoir(s) 24 and labyrinthine channel(s) 28 are realized between a first plastic sheet 38 formed with cavities 39 therein defining growth chamber(s) 22, supplements reservoir(s) 24 and labyrinthine channel(s) 28, and a second, flat, plastic sheet 40 sealed thereto, so as to form growth chamber(s) 22, supplements reservoir(s) 24 and labyrinthine channel(s) 28. Sealing can be effected, for example, by welding, bonding or soldering.

According to a preferred embodiment of the present invention first plastic sheet 38 is constructed such that each of growth chamber(s) 22 and each of supplements reservoir (s) 24 is adapted for holding a liquid therein when first plastic sheet 38 is vertically positioned and when second, flat, plastic sheet 40 is yet unsealed thereto. Alternatively, sheet 38 is constructed such that each of growth chamber(s) 22 and each of supplements reservoir(s) 24 is adapted for holding a liquid therein when first plastic sheet 38 is horizontally positioned and when second, flat, plastic sheet 40 is yet unsealed thereto. These alternative configurations are achieved by shaping cavities 39 appropriately.

According to a preferred embodiment of the present invention, device 20 further includes a provision for media removal in the form of a pierceable region 45. Removal of media may be desirable, for example, to facilitate rinsing of roots with an antiseptic solution immediately prior to planting in the ground. According to additional embodiments of the device of the present invention, this rinsing could be accomplished by using a rinsing solution stored in an additional supplements reservoir. Such an arrangement assures the availability of a supply of sterile rinsing solution in the planting field.

According to another preferred embodiment of the present invention, supplements reservoir 24 is further divided into compartments 24a–c, such that each compartment may contain a separate supplements mixture. According to this embodiment, supplements may be added sequentially beginning with the supplements stored proximally and ending with the supplement stored most distally. Each successive addition is accomplished by squeezing the appropriate compartment 24a–c so that its contents is forced through channel 26 into growth chamber(s) 22.

According to another aspect of the present invention there is provided a method for propagating explant cultures. The method is implemented executing the following method steps, in which, in a first step, a first sheet is provided formed with cavities therein defining at least one growth chamber, at least one supplements reservoir and a labyrinthine channel, being in fluid communication with one another. Then, a growth medium and optionally a plant support matrix is placed in the at least one growth chamber and a supplementary substance in the at least one supplements reservoir. Biological material, such as, but not limited to, at least one plant call, preferably a plurality of plant cells, plant tissue or callus, is thereafter placed in the culture medium. Then, the second sheet is sealed over the first sheet. Following a time period, the growth medium can be supplemented with the supplementary substance while avoiding separation between the first and second sheets. Supplementation can be effected once or by a series of successive supplementations.

According to yet another aspect of the present invention there is provided a process of manufacturing device 20. The process is effected by (a) providing a plastic material; and (b) forcing the plastic material to conform with a contour of a mold which is further described hereinunder, thereby defining at least one growth chamber, at least one supplements reservoir and at least one labyrinthine channel being in fluid communication with one another. Forcing the plastic material to conform with the contour of the mold is preferably effected by a method, such as, but not limited to, vacuum or pressure thermoforming, roller pressing, injection molding and pressing between matching molds. Heat is preferably applied to the plastic material while forcing the plastic material to conform with contour of mold.

Figure 2:
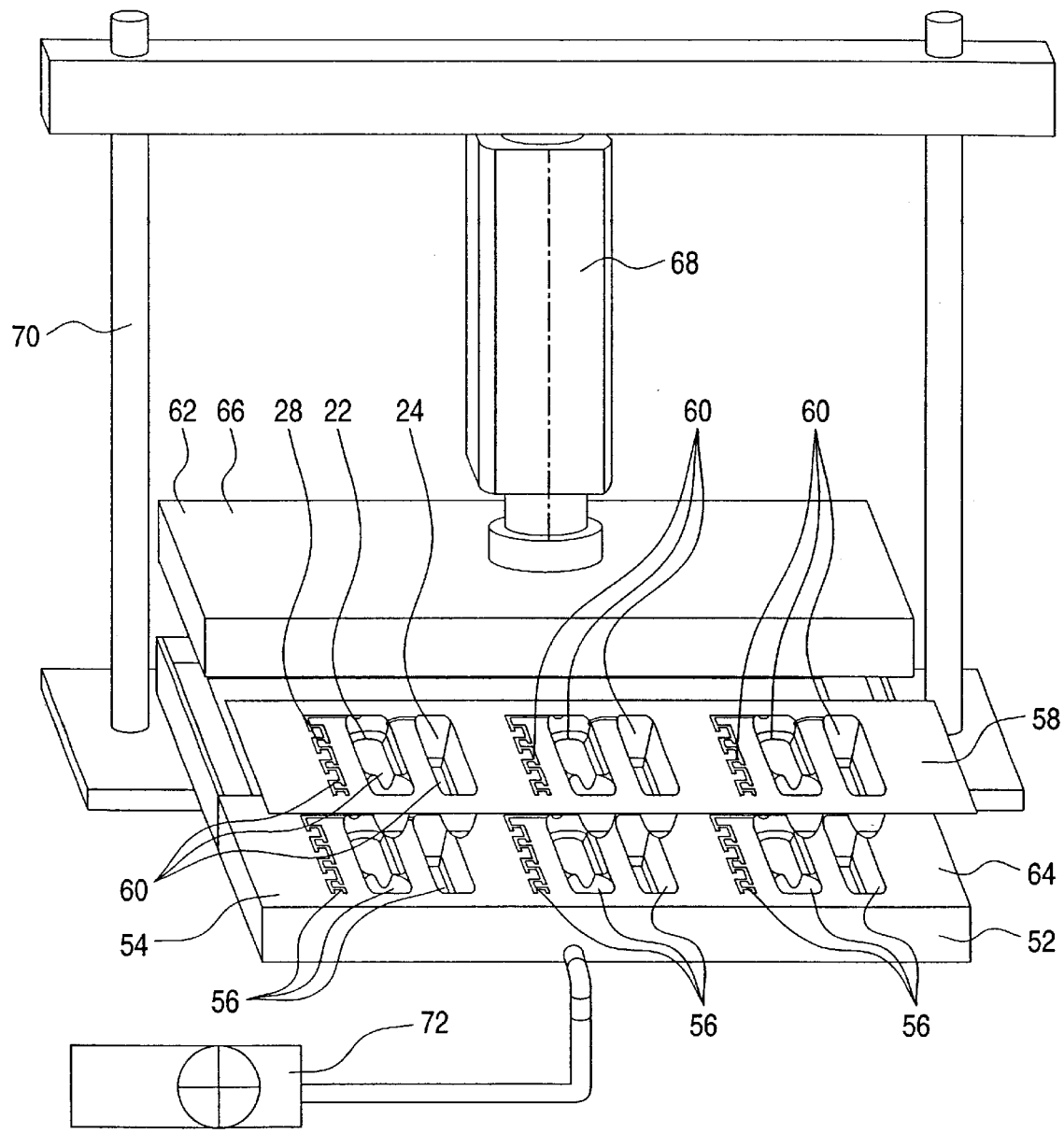
FIG. 2 is a perspective view of an apparatus for manufacturing the device shown in FIG. 1.
Figure 3:
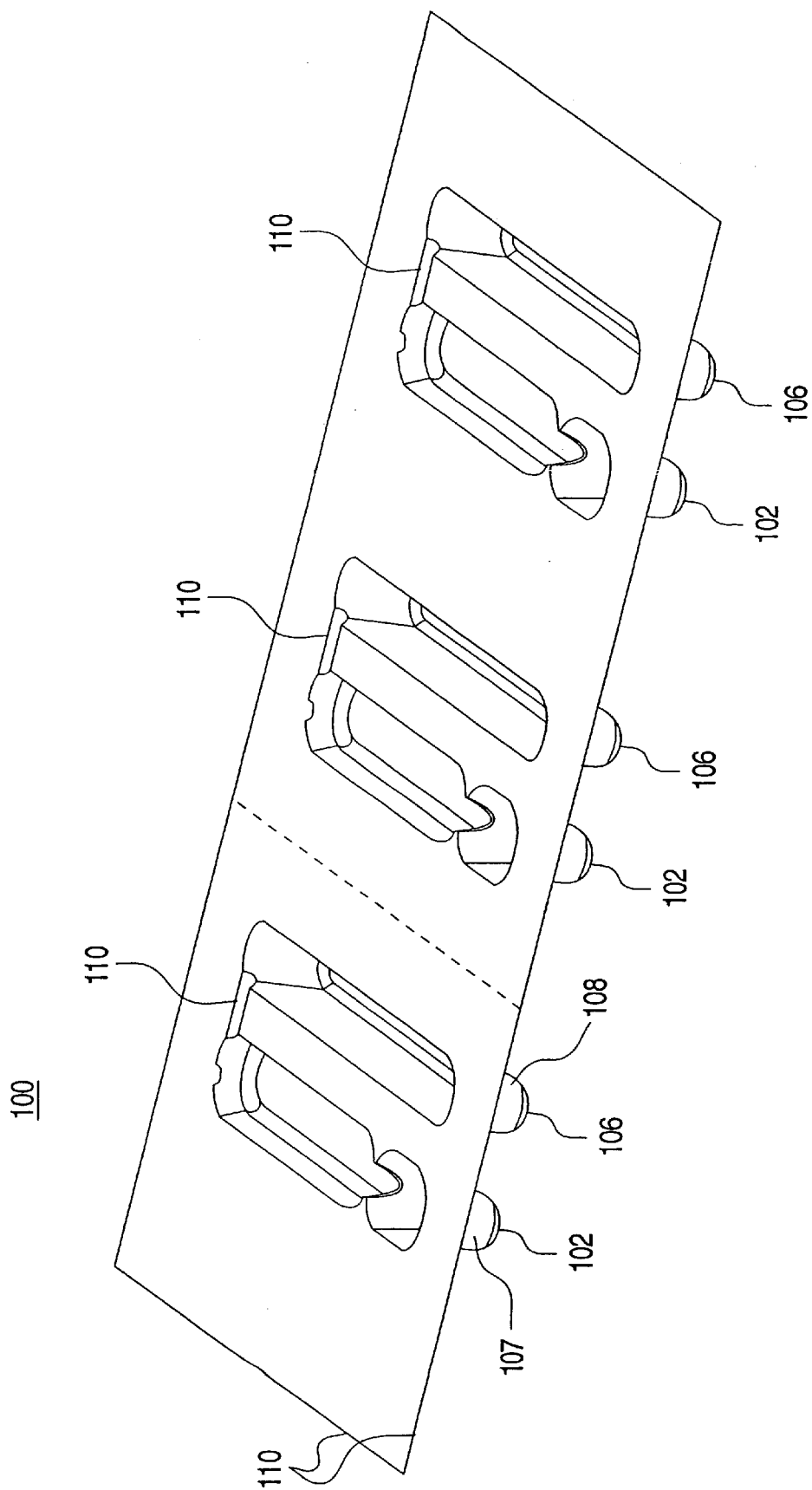
FIG. 3 is a perspective view of a device for propagating explant cultures according to another aspect of the present invention.

According to another aspect of the present invention there is provided an apparatus for manufacturing device 20, which is referred to hereinbelow as apparatus 50. Apparatus 50 includes a mold 52 which has a flat body 54 formed with a plurality of patterns 56 in communication with one another. Patterns 56 are so designed such that by placing a plastic sheet 58 on top of flat body 54 and forcing portions 60 of plastic sheet to conform with patterns 56, plastic sheet 58 deforms to thereby define at least one growth chamber 22, at least one supplements reservoir 24 and at least one labyrinthine channel 28 in fluid communication with one another. Apparatus 50 further includes a mechanism 62 operating with mold 50 and which serves for forcing portions 60 of plastic sheet 58 to conform with patterns 56 of mold 52. According to one embodiment of the present invention patterns 56 protrude from a surface 64 of flat body 54. However, according to a presently preferred embodiment, patterns 56 recess from surface 64 of flat body 54. Mechanism 62 operating with mold 50 and which serves for forcing portions 60 of plastic sheet 58 to conform with patterns 56 of mold 52 can include one or several mechanisms which act in synergy to force portions 60 of plastic sheet 58 to conform with patterns 56 of mold 52. Such mechanisms, can include, for example, a pressure mechanism, a vacuum mechanism, a press mechanism and a heating mechanism. In the example of FIG. 2, a heated press 66 translatable via a pneumatic or hydraulic extendible/retractable arm 68 in relation to a frame 70 holding mold 52 is used in combination with a vacuum mechanism 72 which is in fluid communication with recessed patterns 56, to thereby collectively force portions 60 of plastic sheet 58 to conform with patterns 56 of mold 52.

According to another aspect of the present invention there is provided a device for propagating explant cultures, which is referred to hereinbelow as device 100. Device 100 includes at least one growth chamber 102 which serves for containing and retaining therein a culture medium 104. Device 100 further includes a gas permeable, liquid impermeable membrane 104 sealing growth chamber(s) 102. Membrane 104 serves for restricting liquids in device 100, while, at the same time, facilitating aeration, yet restricting contamination by airborne contaminants such as bacteria and viruses. Membrane 104 can, for example, be made of, or include, a fluorocarbon polymer known a TEFLON. According to a preferred embodiment of the present invention device 100 further includes at least one supplements reservoir 106 which serves for containing and retaining therein at least one supplementary substance 108 as defined hereinabove. Supplements reservoir(s) 106 are provided in fluid communication via channels 110 with growth chamber(s) 102, such that, when so required, supplementary substance (s) 108 are addable to growth chamber(s) 102. The operation of device 100 is very similar to that of device 20. Membrane 104 provides the functionalities of second sheet 40 and as labyrinthine channels 28 (FIG. 1). Therefore, all the other features described with respect to device 20 apply also to device 100, including, but not limited to, fluid communication of different types between growth chambers, assembly formation and perforations, sealing the membrane by welding, bonding or soldering, providing the growth chamber(s) adapted for holding a liquid therein when vertically or horizontally positioned and when gas permeable, liquid impermeable membrane, is yet unsealed thereto, and the like.

According to another aspect of the present invention there is provided a method which utilizes device 100 for propagating explant cultures. The method is effected by implementing the following method steps, in which, in a first step, at least one growth chamber is provided and growth medium is placed therein. Biological material is then placed in the medium and the growth chambers are sealed with a gas permeable, liquid impermeable membrane. The method according to this aspect of the present invention preferably further includes the steps of providing at least one supplements reservoir in fluid communication with at least one growth chamber; placing at least one supplementary substance in the at least one supplements reservoir, wherein the step of sealing the at least one growth chamber with the gas permeable, liquid impermeable membrane is effected so as to seal also least one supplements reservoir with gas permeable, liquid impermeable membrane; and following a time period, supplementing the growth medium with at least one of the supplementary substances while the gas permeable, liquid impermeable membrane remains sealed and intact.

According to another aspect of the present invention there is provided a process of manufacturing device 100. The process is effected by forcing a plastic material to conform with a contour of a mold, thereby defining at least one growth chamber and at least one supplements reservoir in fluid communication with one another. Additional features of this process are similar to those described with respect to the process of manufacturing device 20 above and are therefore not repeated herein.

An apparatus which can be used to manufacture device 100 is very similar to apparatus 50 described hereinabove in respect to manufacturing device 20, the difference being that the patterns associated with the formation of the labyrinthine channels are removed, as such channels are no longer required, as further detailed above.

As shown in FIGS. 4–7, according to still another aspect of the present invention there is provided a device for propagating explant cultures, which is referred to hereinbelow as device 200. Device 200 includes a plate 202 which has a first circumference profile 204. Plate 202 is formed with at least one growth chamber 203 which serves for containing and retaining therein a culture medium 206 and optionally also a support matrix. Plate 202 further includes at least one supplements reservoir 208 which serves for containing and retaining therein at least one supplementary substance 210. Supplements reservoir(s) 208 are in fluid communication with growth chamber(s) 203, such that, when so required, supplementary substance(s) 210 are addable to growth chamber(s) 203. In one embodiment shown in FIG. 6, a dispenser 209 is formed with or placed in reservoir 208. By squeezing from the outside, or by tilting device 200 one can dispense the contents thereof Device 200 further includes a cover 220 which serves for covering plate 202. Cover 220 is formed with a second circumference profile 222. First circumference profile 204 and second circumference profile 222 are constructed so as to form a circumferential labyrinthine passage 224 between plate 202 and cover 220 when plate 202 is covered by cover 220. Circumferencial labyrinthine passage 224 communicates between growth chamber(s) and an atmosphere and serves for aeration while at the same time for preventing contamination.

Additionally, and according to a preferred embodiment, first circumference profile 204 and second circumference profile 222 are constructed so as to secire or lock together plate 202 and cover 220 when plate 202 is covered by cover 220 in a way which does not interfere with the functionality labyrinthine passage 224.

Figure 4:
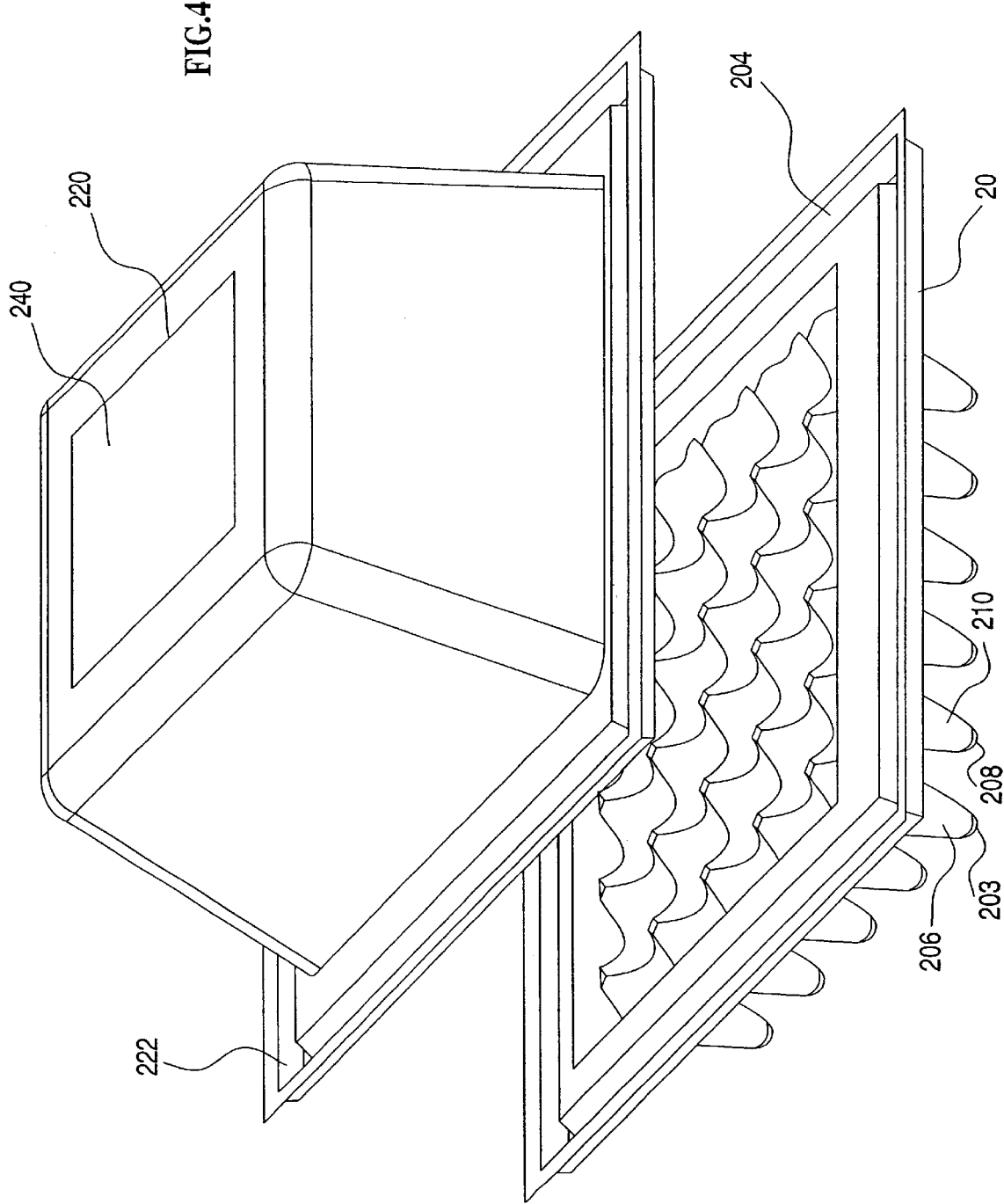
FIG. 4 is a perspective view of a device for propagating explant cultures according to yet another aspect of the present invention showing several additive or alternative embodiments which are not necessarily integrated into a single device, showing a plate and a removable cover.
Figure 5:
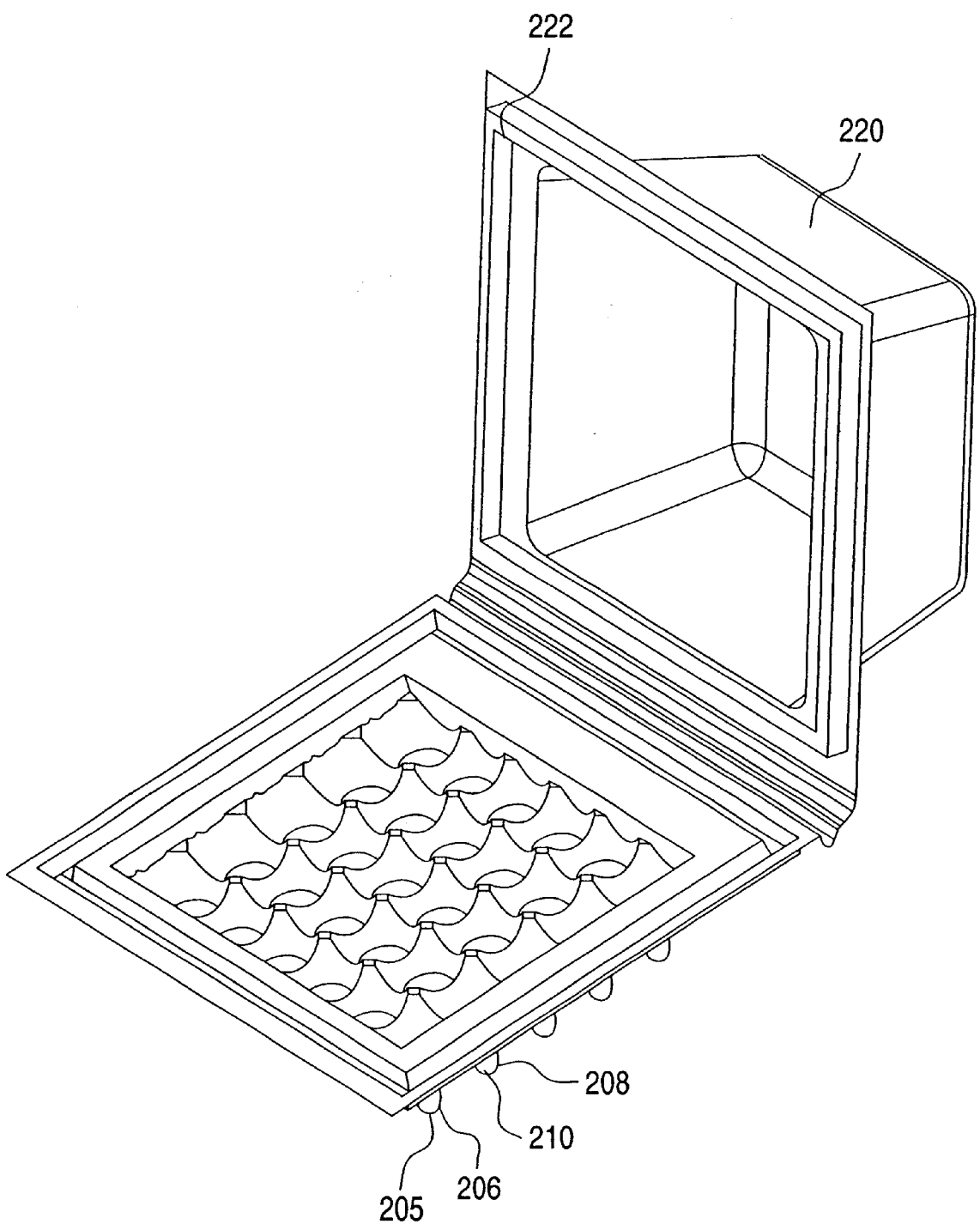
FIG. 5 is a perspective view of one embodiment of the device of FIG. 4, showing a plate coverable by a cover connected thereto via an integral hinge.
Figure 6:
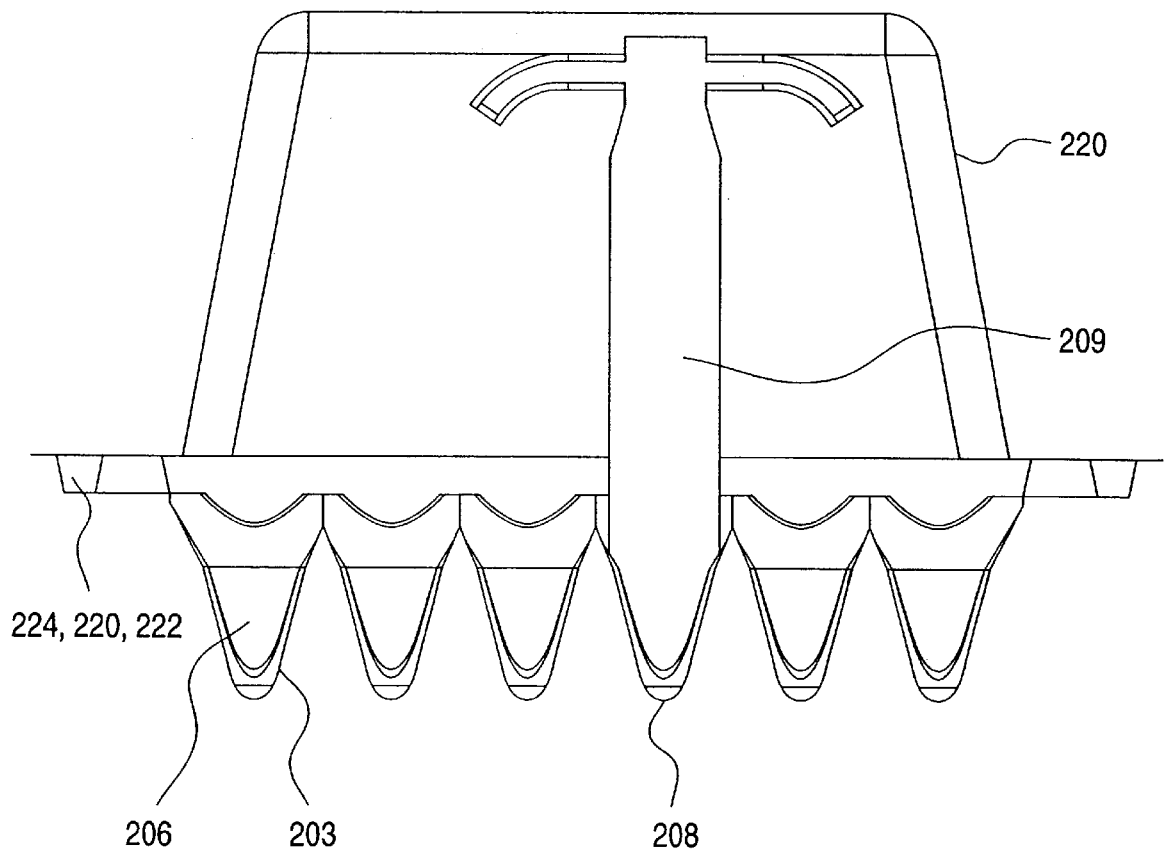
FIG. 6 is a cross sectional view of another embodiment of the device of FIG. 4.
Figure 7:
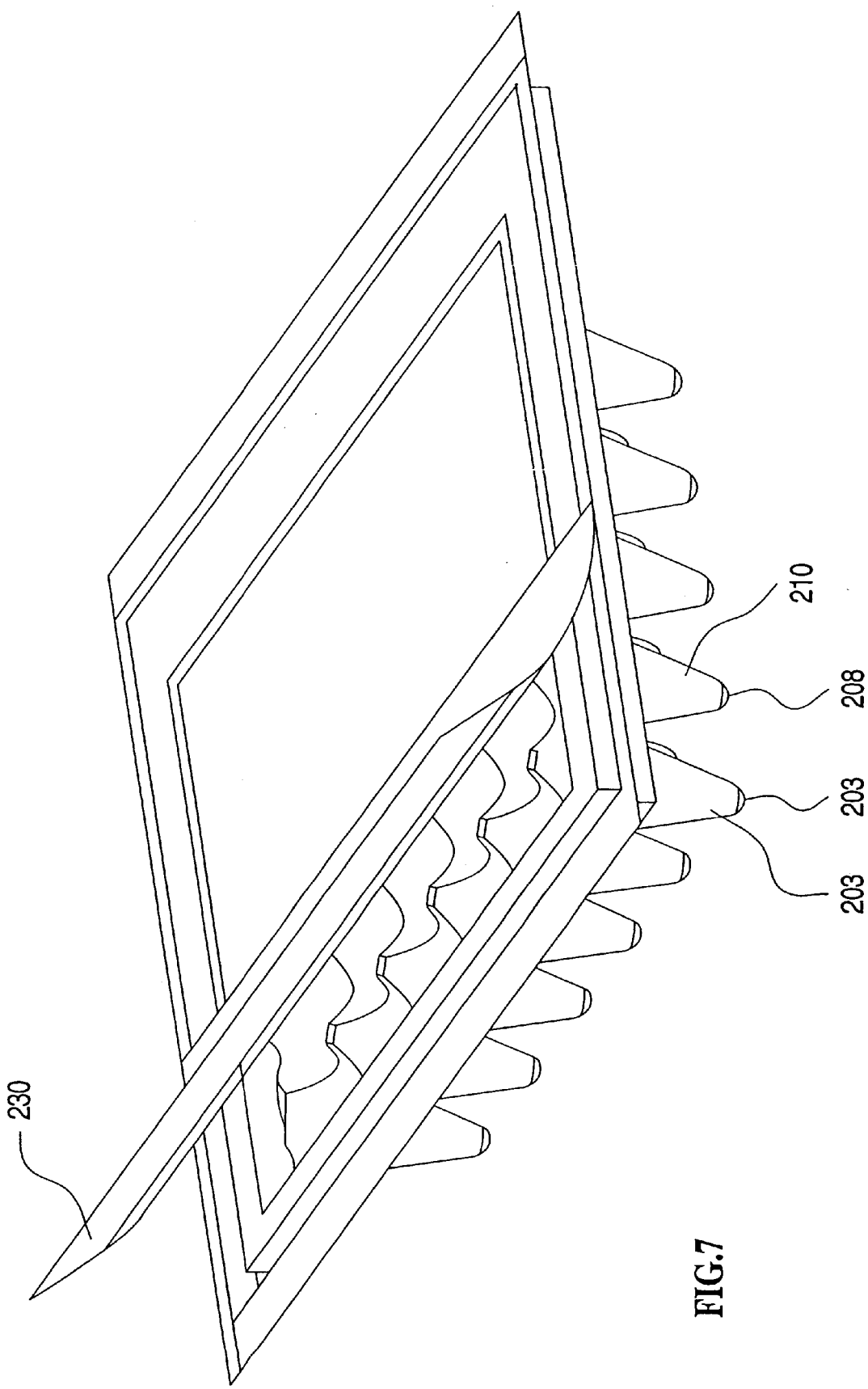
FIG. 7 is a perspective view of yet another embodiment of the device of FIG. 4, showing a plate sealed with a removable seal.

As shown in FIGS. 4–7, growth chambers 203 are in fluid communication with one another through medium non-containing portions thereof. However, in other configurations growth chambers 203 are provided in fluid communication with one another through medium containing portions thereof. Cover 220 can be separable from plate 202, as for example shown in FIG. 4. In this case, as shown in FIG. 7, a removable seal 230 is preferably provided on top of plate 202, for preventing contamination prior to use, which seal 230 is removed upon use and is replaced by cover 220. Alternatively, plate 202 can be provided within a sterile bag. However, as shown in FIG. 5, cover 220 can be attached to container 202 by means of an integral hinge. Plate 202 and/or cover 220 are preferably designed stackable so as to reduce shipment/storage volume when supplied medium free. As shown in FIG. 4, a gas permeable, liquid impermeable membrane 240 can be integrated in cover 220 and serve to replace circumferencial labyrinthine passage 224 in aeration and prevention of contamination.

According to another aspect of the present invention there is. provided a method for propagating explant cultures using device 200. The method is effected by (a) providing a plate formed with at least one growth chamber and at least one supplements reservoir being in fluid communication with one another; (b) placing a growth medium and optionally also a support matrix in the at least one growth chamber; (c) placing at least one supplementary substance in the at least one supplements reservoir; (d) providing a biological material in the at least one culture medium; (e) covering the plate with a cover so as to form a circumferencial labyrinthine passage between the plate and the cover, the circumferencial labyrinthine passage communicating between the at least one growth chamber and an atmosphere; and (f) following a time period, supplementing the growth medium with at least one of the supplementary substances while avoiding removing the cover from the plate.

Thus, the present invention provides a low cost device for explant culture, which facilitates growth under sterile conditions and allows aseptic addition or change of culture medium without benefit of a laminar flow hood. Such a device allows performance of routine explant propagation by unskilled personnel in facilities with a minimum of equipment. Additionally, molds and apparatuses incorporating same allow construction of the aforesaid device to be undertaken easily at or near the intended point of use.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A device for propagating explant cultures, the device comprising:

(a) at least one growth chamber for containing and retaining therein a culture medium; and (b) a gas permeable, liquid impermeable membrane sealing said at least one growth chamber;

wherein said at least one growth chamber includes a plurality of growth chambers, whereas said plurality of growth chambers are in fluid communication with one another through medium non-containing portions thereof.

2. An assembly comprising a plurality of units each of said plurality of units including a device for propagating explant cultures, the device comprising:

(a) at least one growth chamber for containing and retaining therein a culture medium; and (b) a gas permeable, liquid impermeable membrane sealing said at least one growth chamber;

wherein said at least one growth chamber retains a plant support matrix selected from the group consisting of agar, agarose, a polyurethane foam, a non-woven polypropylene fiber, glass beads, a microporous polypropylene membrane, a polypropylene netting, polyacrylamide beads, super absorbent gel, vermiculite and soil, wherein at least some of said plurality of units are separated therebetween via perforations.

3. A device for propagating explant cultures, the device comprising:

(a) at least one growth chamber for containing and retaining therein a culture medium; and (b) a gas permeable, liquid impermeable membrane sealing said at least one growth chamber, constructed such that each of said at least one growth chamber is adapted for holding a liquid therein when vertically positioned and when said gas permeable, liquid impermeable membrane, is yet unsealed thereto.

* * * * *